United States Patent
Juo et al.

(10) Patent No.: US 11,040,055 B2
(45) Date of Patent: Jun. 22, 2021

(54) METHOD OF TREATING DIABETIC RETINOPATHY OR WET TYPE ADULT MACULAR DEGENERATION

(71) Applicant: China Medical University, Taichung (TW)

(72) Inventors: Suh-Hang Hank Juo, Taichung (TW); Chung-Ling Liang, Taichung (TW); Tzu-Ming Wang, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 16/469,962

(22) PCT Filed: Dec. 12, 2017

(86) PCT No.: PCT/US2017/065661
§ 371 (c)(1),
(2) Date: Jun. 14, 2019

(87) PCT Pub. No.: WO2018/111784
PCT Pub. Date: Jun. 21, 2018

(65) Prior Publication Data
US 2019/0321389 A1  Oct. 24, 2019

Related U.S. Application Data

(60) Provisional application No. 62/434,409, filed on Dec. 14, 2016.

(51) Int. Cl.
| | |
|---|---|
| *C07H 21/04* | (2006.01) |
| *A61K 48/00* | (2006.01) |
| *A61K 31/7105* | (2006.01) |
| *A61P 27/02* | (2006.01) |
| *A61K 9/00* | (2006.01) |
| *A61K 47/32* | (2006.01) |
| *C12N 15/113* | (2010.01) |
| *A61K 9/127* | (2006.01) |
| *A61K 45/06* | (2006.01) |

(52) U.S. Cl.
CPC ........ *A61K 31/7105* (2013.01); *A61K 9/0051* (2013.01); *A61K 47/32* (2013.01); *A61P 27/02* (2018.01); *C12N 15/113* (2013.01); *A61K 9/127* (2013.01); *A61K 45/06* (2013.01); *C12N 2310/141* (2013.01); *C12N 2320/30* (2013.01)

(58) Field of Classification Search
CPC ................ A61K 31/713; C12N 15/113; C12N 2310/141
See application file for complete search history.

(56) References Cited

U.S. PATENT DOCUMENTS 9,096,850 B2 * 8/2015 Chorn ............... C12N 15/111
9,315,812 B2 4/2016 Juo et al.
2012/0014970 A1 1/2012 Dana et al.
2016/0158320 A1 1/2016 Schultz et al.
2016/0215285 A1 * 7/2016 Russell .............. C12N 15/113

FOREIGN PATENT DOCUMENTS

| WO | 2016123556 A1 | 8/2016 | |
|---|---|---|---|
| WO | WO 2016/123556 A1 * | 8/2016 | ........... A61K 31/713 |
| WO | 2016144766 A1 | 9/2016 | |
| WO | 2016151287 A1 | 9/2016 | |

OTHER PUBLICATIONS

Mortuza et al. (Diabetologia, 2014, 57, 1037-1046).*
Zhao et al. (Nature Communications, 2016, 7, pp. 1-9).*
Zhang et al. (J. Cell. Mol. Med., 12, 1, 2008, 3-21).*
Mortuza ("Role of SIRT1 in Vascular Complications of Diabetes" (2014). Electronic Thesis and Dissertation Repository. 2457).*
McKiernan et al. (Int J Nanomedicine, 2013, 8, 3907-3915.*
Bian, Fang, et al., "Dexamethasone Drug Eluting Nanowafers Control Inflammation in Alkali-Burned Corneas Associated With Dry Eye", Investigative ophthalmology & visual science, published by the Association for Research in Vision and Ophthalmology, United States, published in Jun. 2016, pp. 3222-3230.
Cerani, Agustin, et al., "Neuron-Derived Semaphorin 3A Is an Early Inducer of Vascular Permeability in Diabetic Retinopathy via Neuropilin-1", Cell Metabolism—published by Elsevier Inc, Oct. 1, 2013, pp. 505-518.
Chen, Na, et al., "MicroRNA-410 Reduces the Expression of Vascular Endothelial Growth Factor and Inhibits Oxygen-Induced Retinal Neovascularization", PLOS one—Public Library of Science, Apr. 28, 2014, pp. 1-8.
Chen, Hongming, "Recent developments in ocular drug delivery", Journal of Drug Targeting—Informa, United Kingdom, 2015, pp. 597-604.
Ciolino, Joseph B., et al., "Latanoprost-Eluting Contact Lenses in Glaucomatous Monkeys", American Academy of Ophthalmology—, published by Elsevier Inc., United States, Oct. 2016, pp. 2085-2092.
Hsu, K. H., et al., "Review of ophthalmic drug delivery by contact lenses", Journal of Drug Delivery Science and Technology—published by Elsevier B.V., Netherlands, published in 2014, pp. 123-135.
Kim, Jean, et al. "Nanostructured materials for ocular delivery: nanodesign for enhanced bioadhesion, transepithelial permeability and sustained delivery", Therapeutic Delivery—published by Future Science Group, United Kingdom, Dec. 2015, pp. 1365-1376.
Kirchhof, Susanne, et al., "Hydrogels in ophthalmic applications", European Journal of Pharmaceutics and Biopharmaceutics—published by Elsevier B.V., Netherlands, Sep. 2015, pp. 227-238.
Mortuza, Rokhsana, et al., "miR-195 regulates SIRT1-mediated changes in diabetic retinopathy", Diabetologia—, published by Springer-Verlag, Germany., May 2014, pp. 1037-1046.
Phan, Chau-Minh, et al., "In vitro uptake and release of natamycin Dex-b-PLA nanoparticles from model contact lens materials", Journal of Biomaterials Science, Polymer Edition—published by Informa, United Kingdom, published in 2014, pp. 18-31.

(Continued)

*Primary Examiner* — Amy H Bowman

(57) ABSTRACT

Methods and compositions for treating diabetic retinopathy employ an ophthalmic, topical formulation of micro-RNA 195 packaged in or on a nanoparticle or vesicle.

9 Claims, 3 Drawing Sheets

(56) References Cited

OTHER PUBLICATIONS

Phan, Chau-Minh, et al., "Release of Moxifloxacin from Contact Lenses Using an In Vitro Eye Model: Impact of Artificial Tear Fluid Composition and Mechanical Rubbing", Translational vision science & technology—published by the Association for Research in Vision and Ophthalmology, United States, Nov. 2016, pp. 1-10.
Wang, Yung-Song, et al., "MicroRNA-195 regulates vascular smooth muscle cell phenotype and prevents neointimal formation", Cardiovascular Research—published by Oxford University Press, United Kingdom., Sep. 1, 2012, pp. 517-526.
Yandrapu, Sarath, et al., "Development of Sustained-Release Microspheres for the Delivery of SAR 1118, an LFA-1 Antagonist Intended for the Treatment of Vascular Complications of the Eye", Journal of Ocular Pharmacology and Therapeutics—published by Mary Ann Liebert, Inc., United States, Mar. 13, 2013, pp. 236-248.
Zhao, Yi et al., "PolyMetformin combines carrier and anticancer activities for in vivo siRNA delivery", Nature Communications—, published by Nature Publishing Group, United Kingdom, Jun. 6, 2016, pp. 1-9.
Shiyue, Qin, et al., "The expression and role of miR-195 in diabetic retinopathy", Chinese Journal of Ocular Fundus Diseases, published on Mar. 25, 2015, vol. 31, No. 2, pp. 134-138, published by West China Hospital of Sichuan University, China, P.R.C.

\* cited by examiner

METHOD OF TREATING DIABETIC RETINOPATHY OR WET TYPE ADULT MACULAR DEGENERATION

CROSS REFERENCE TO RELATED APPLICATIONS

This is the National Phase entry of International Application No. PCT/US2017/065661, filed Dec. 12, 2017, which claims priority to U.S. Application No. 62/434,409, filed Dec. 14, 2016, the disclosures of which are incorporated herein by reference in their entireties.

INTRODUCTION

Diabetic retinopathy (DR) is currently treated with intra-ocular injection of anti-VEGF drugs, ranibizumab (Lucentis®) and bevacizumab (Avastin®). The underlying rationale is that late stage DR presents new blood vessel formation that causes edema in the ocular fundus.

sema3A is an early inducer for DR (Cerani A et al. Neuron-derived semaphorin 3A is an early inducer of vascular permeability in diabetic retinopathy via neuropilin-1. Cell Metab. 2013 Oct. 1; 18(4):505-18). sema3A is produced in retinal neural cells, which promotes blood vessel permeability leading to retinal edema that is a characteristic of DR.

We previously reported that miR-195 can suppress sema3A expression resulting in certain neuroprotective effects (U.S. Pat. No. 9,315,812), and that microRNA-195 can suppress inflammation (Wang et al. MicroRNA-195 regulates vascular smooth muscle cell phenotypes and prevents neointimal formation. Cardiovasc Res. 95(4): 517-26, 2012).

miR-195 has been reported to regulate SIRT1-mediated changes in diabetic retinopathy, Mortuza et al., Diabetologia. 2014 May; 57(5):1037-46. This group reported that high glucose caused increased miR-195 levels and decreased SIRT1 expression in both HRECs and HMECs. Transfection with miR-195 antagomir and forced expression of SIRT1 prevented such changes, whereas transfection with miR-195 mimic produced high glucose-like effects A microRNA-410 has been reported to reduce the expression of VEGF and inhibits oxygen-induced retinal neovascularization by topically delivering the microRNA's gene (DNA), Chen et al., PLoS One. 2014; 9(4): e95665. MicroRNA-410.

WO 2016151287 discloses treatment of preeclampsia using miR-122, miR-374b or inhibitors of miR-152 or miR195

SUMMARY OF THE INVENTION

In an aspect the invention provides an ophthalmic, topical formulation of micro-RNA 195.

In embodiments, the micro-RNA is packaged in or on a particle or vesicle selected from a liposome delivery system (such as dicetyl phosphate-tetraethylenepentamine-based polycation liposomes (TEPA-PCL), lipoplexes, like DOTMA:cholesterol: TPGS lipoplexes, DDAB:cholesterol: TPGS lipoplexes), cationic liposome-hyaluronic acid (LPH) nanoparticles), a polyethyleneimine (PEI) or PEI-conjugate, dendrimers, poly(amidoamine), poly (lactide-co-glycolide) (PLGA) nanoparticles, atelocollagen, exosomes, and silica nanoparticles;

the micro-RNA is packaged in or on a particle or vesicle that is a PEI conjugate that is a conjugation of linear polyethylenimine (PEI) with dicyandiamide to form polymetformin;

the micro-RNA is at a concentration of 0.1-1000 uM or 1-100 uM;

the formulation is in the form of an ophthalmic gel, ointment, suspension or solution. (lubricant);

the formulation is in the form of a polymeric solid or semi-solid formulation selected from a membrane or lens, wafer or microspheres;

the formulation is in the form a polymeric solid or semi-solid formulation that is a hydrogel contact lens;

the formulation is in unit dosage form, such as a loaded contact lens, eye drop, depot or bollus;

the formulation is packaged in an eye drop dispenser (such as eye drop bottle, pipette, etc.);

the formulation further comprises excipients and features suitable for direct, topical delivery to the eye, including opthalmically suitable clarity, pH buffer, tonicity, viscosity, stability, sterility, etc.; and/or the formulation further comprises another, different ophthalmic drug, particularly an anti-retinopathy, anti-AMD, or anti-VEGF drug, particularly an anti-diabetic retinopathy drug;

In another aspect, the invention provides a method of using a disclosed formulation, comprising administering the formulation to an eye in need thereof, such as of a patient suffering from an ocular pathology, such as AMD or a retinopathy, such as diabetic retinopathy.

In another aspect the invention provides a method of treating an eye in need thereof, the method comprising topically delivering to the eye micro-RNA 195.

In embodiments:

the eye is determined to be afflicted with an ocular disease or pathology, particularly retinal pathology, such as diabetic retinopathy, or adult macular degeneration (AMD), particularly wet type AMD which is also treated with anti-VEGF, or traumatic head injury which has been associated with retinal damage/degeneration . . . ) ; and/or the method further comprises detecting a resultant improvement of the eye or diminution of the ocular disease or pathology.

The invention encompasses all combination of the particular embodiments recited herein, as if each combination had been laboriously recited.

Figure 1:
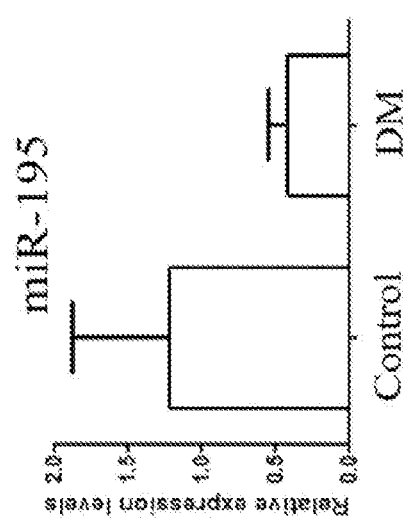
FIG. 1. microRNA-195 (miR-195) levels were reduced by more than 50% in the eyes of diabetic rats.

DESCRIPTION OF PARTICULAR
EMBODIMENTS OF THE INVENTION

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

The invention provides topical ophthalmic methods and compositions for treating diabetic neuropathy with microRNA 195, particularly in the form of form of an ophthalmic gel, ointment, suspension or solution, such as a polymeric solid or semi-solid formulation, like a membrane or lens, wafer or microspheres, and particularly in the form a polymeric solid or semi-solid formulation like a hydrogel contact lens.

Materials and methods for making such formulations are exemplified herein, and/or known in the art; for example, hydrogels in ophthalmic applications are reviewed in Kirchhof, Eur J Pharm Biopharm. 2015 Sep.;95(Pt B):227-38, and recent developments in ocular drug delivery are reviewed in Chen, J Drug Target. 2015; 23(7-8):597-604.

Applicable protocols for manufacturing, loading and delivering drugs in gel materials like contacts lenses and wafers are well-known in the art, e.g. Hsu et al., 2014, J Drug Deliv Sci Tech 24(2), 123-35, Review of ophthalmic drug delivery by contact lenses.

Applicable polymeric controlled release microspheres (eg. Yandrapu et al., J Ocul Pharmacol Ther. 2013 Mar.; 29(2): 236-248), based on biodegradable polymers such as poly (lactic acid) (PLA), poly(glycolic acid) (PGA), and their copolymers, poly(lactic-co-glycolic) acid (PLGA) are known, as are applicable nanoparticles and nanostructured materials, e.g. Kim et al., Ther Deliv. 2015 Dec.; 6(12): 1365-1376; Ciolino et a., Opthalmology 2016, 123 (10), 2085-92; Nanoparticles J Biomater Sci Polym Ed. 2014; 25(1):18-31; Bian et al. Invest Ophthalmol Vis Sci. 2016 Jun.; 57(7): 3222-3230).

A topical solution containing miRNA-195 can contain a physiologically compatible vehicle, as those skilled in the ophthalmic art can select using conventional criteria. The ophthalmic vehicles include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

The formulation optionally includes a preservative, such as benzalkonium chloride and other inactive ingredients such as EDTA. However, for chronic (over two weeks) use, preferred formulations are those without any preservatives due to the potential for damage to the corneal epithelium that may result from long term, frequent exposure to preservatives such as benzalkonium chloride. The formulations without preservatives are prepared in a unit dose and stored in a single-use container.

The pH of the formulation is adjusted by adding any physiologically and ophthamologically acceptable pH adjusting acids, bases or buffers to within the range of about 5 to 7.5, preferably 6 to 7. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethyl-amino-methane), and the like. Salts and buffers include citrate/dextrose, sodium bicarbonate, ammonium chloride and mixtures of the aforementioned acids and bases.

The osmotic pressure of the aqueous ophthalmic composition is generally from about 200 to about 400 milliosmolar (mOsM), more preferably from 260 to 340 mOsM. The osmotic pressure can be adjusted by using appropriate amounts of physiologically and ophthamologically acceptable ionic or non-ionic agents. Sodium chloride is a preferred ionic agent, and the amount of sodium chloride ranges from about 0.01% to about 1% (w/v), and preferably from about 0.05% to about 0.45% (w/v). Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can be used in addition to or instead of sodium chloride to achieve osmolality within the above-stated range. Further, non-ionic agents such as mannitol, dextrose, sorbitol, glucose and the like can also be used to adjust the osmolality.

EXAMPLES

1. Formulation. The following examples employed our miR-195 product called SEMA001. To promote stability and protection from RNAase, the microRNAs are preferably protected or encapsulated by vehicles such as nanoparticles and micro-vesicles, including liposome and polyethylenimine (PEI) polymer. We validated a variety formulation and found a PEI conjugate that is a conjugation of linear polyethylenimine (PEI) with dicyandiamide to form polymetformin ("polymet") to be particularly suitable in our applications; see also, Zhao et al., Jun. 6, 2016, Nature Communications 7:11822; WO2016144766A).

2. We initially measured and determined by real time PCR that microRNA-195 (miR-195) levels were reduced by more than 50% in the eyes of diabetic rats; see, FIG. 1.

3. Intra-ocular (intra-vitreal) injection

We induced diabetics in Sprague Dawley (SD) rats, and then intravitreally injected SEMA001 miR-195 loaded polymet, in addition to opthalmologically acceptable excipients. See, FIG. 2.

Figure 2:
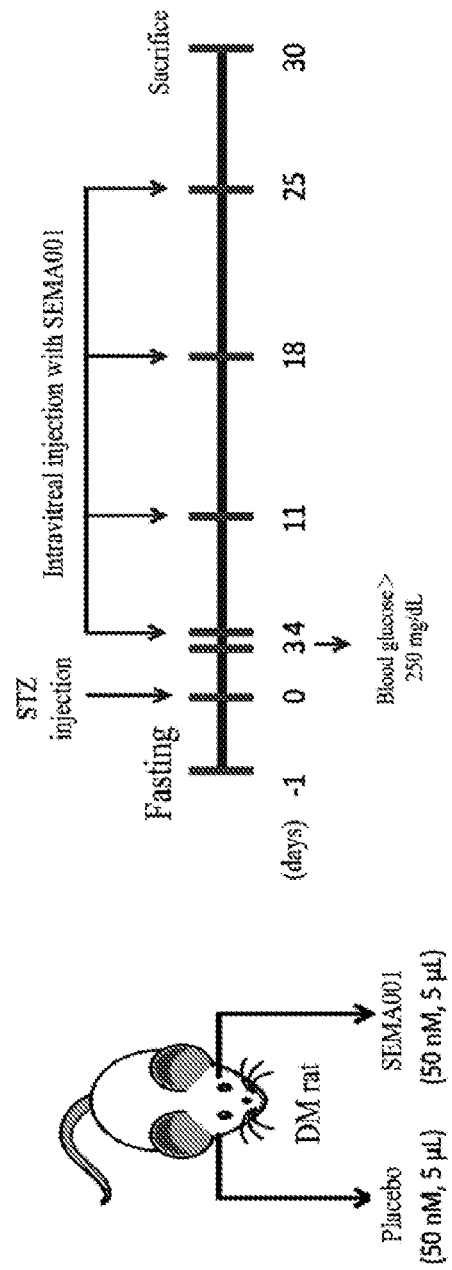
FIG. 2. Intra-ocular (intra-vitreal) injection protocol.
Figure 3:
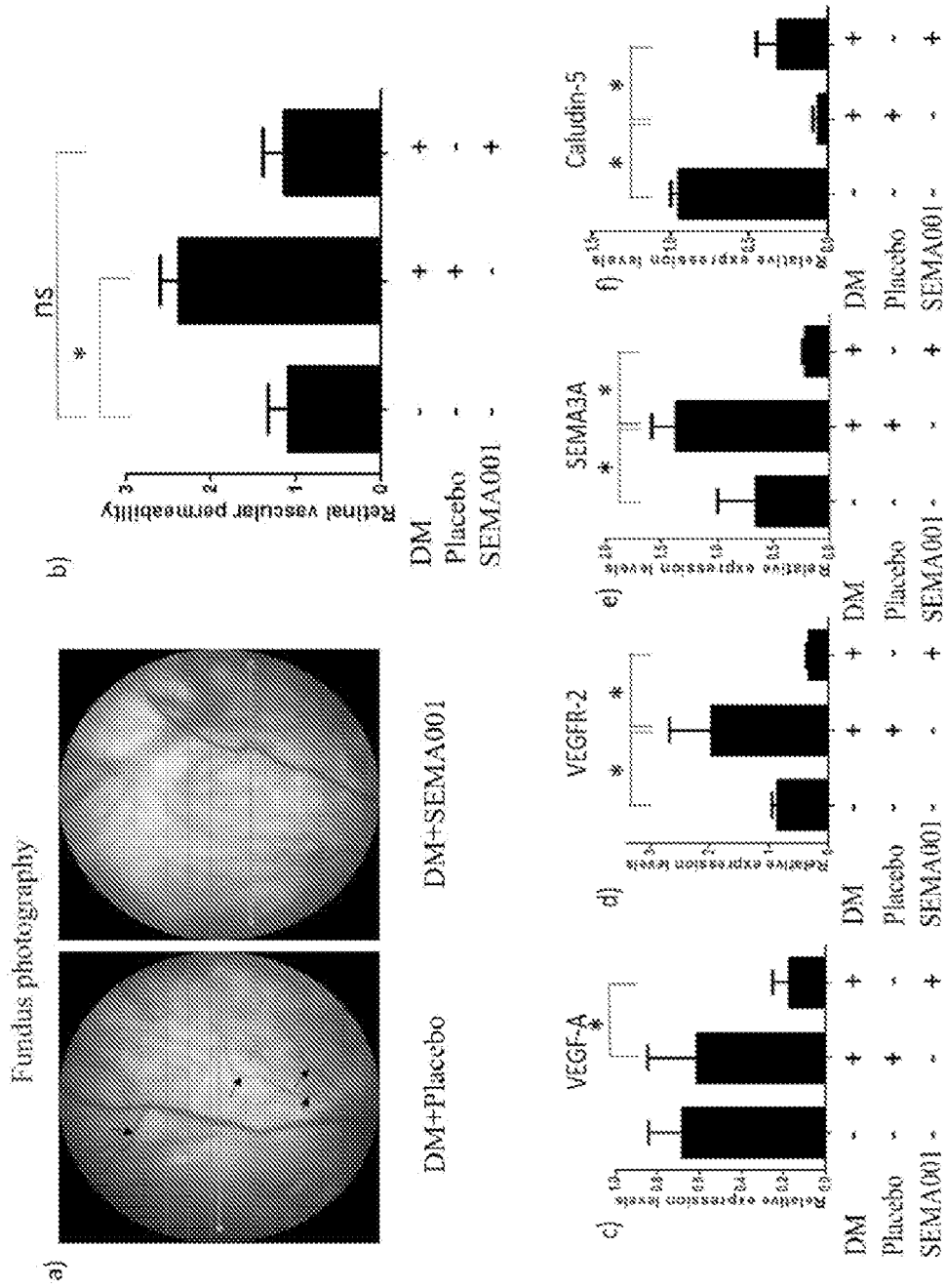
FIGS. 3a-3f. (a) Eye fundus image shows that blood vessels in the rats receiving placebo (polymet+negative control microRNA) than the rats receiving SEMA001 (microRNA-195 nanoparticle formulation). (b) intra-vitreal injection of SEMA001 completely suppressed extravasation (comparing the 3rd bar with 1st bar). ns: no statistical difference (c-d) intra-vitreal injection of SEMA001 reduced the VEGFA and VEGFR2 levels, (e) reduced the sema3A levels and (f) recovered tight junction claudin-5 levels. *p<0.05.
Figure 4:
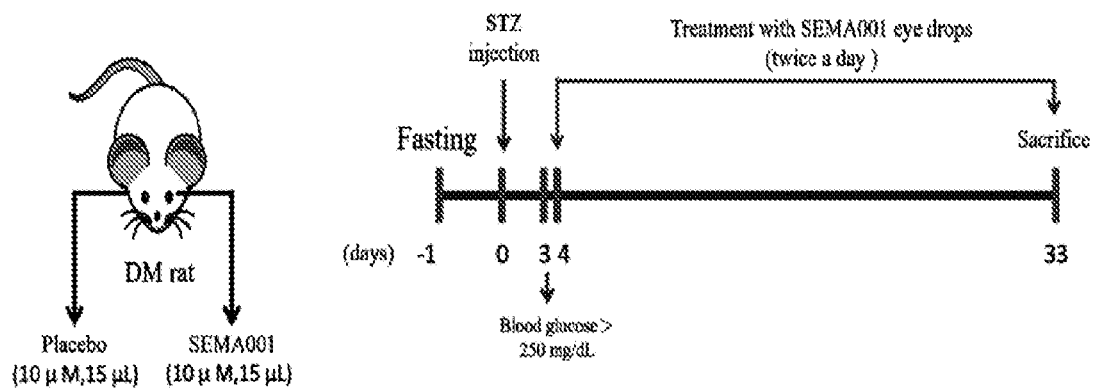
FIG. 4 Topical ocular administration protocol
Figure 5:
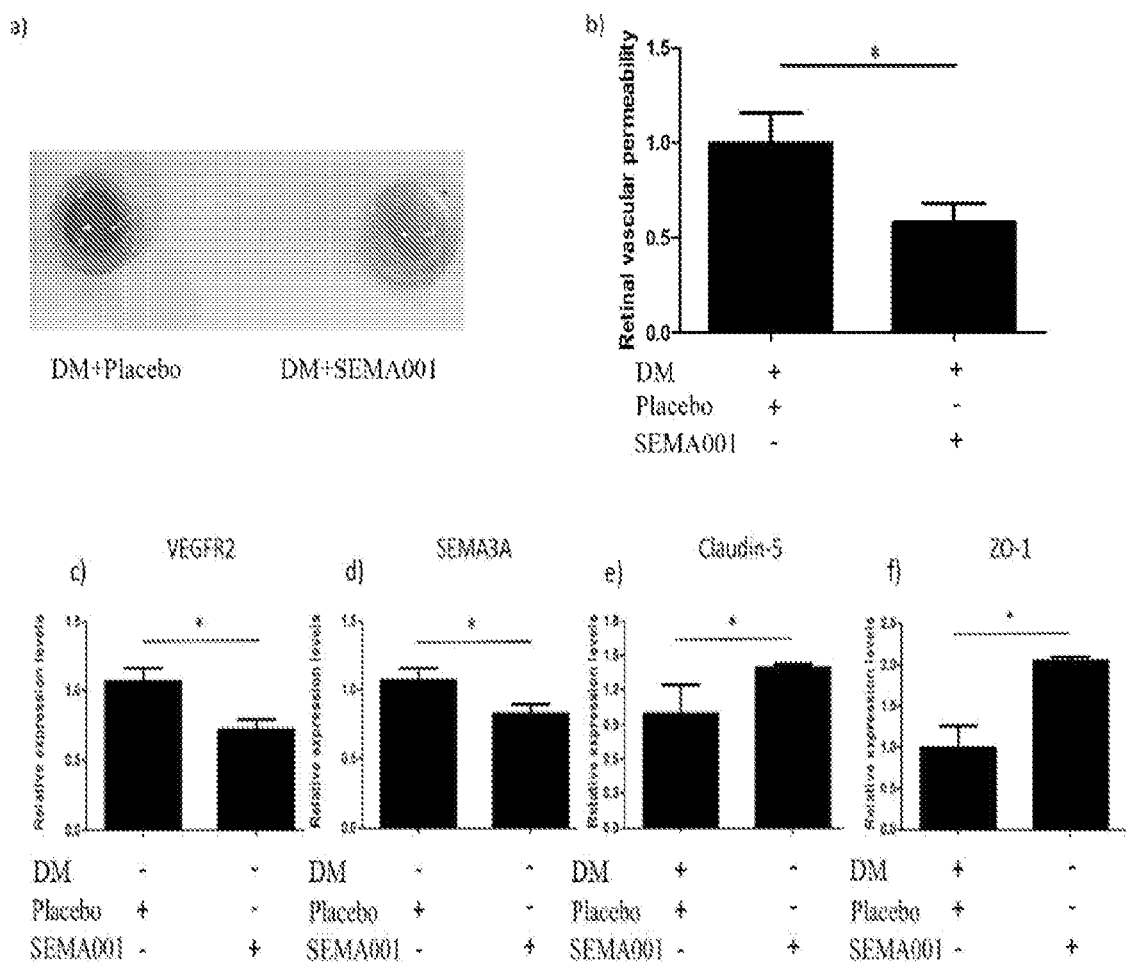
FIGS. 5a-5f. (a) A pair of representative eyes is shown. The eye of more extravasation presents darker blue. That means, the lighter the better. (b) we quantified the amount of extravasation and the results showed SEMA001 eyedrop can reduce extravasation. This result shows that SEMA001 eyedrop effect is comparable to SEMA001 intra-vitreal injection. (c)SEMA001 eyedrop reduced VEGFR2 levels, (d) reduced the sema3A levels and (e-f) recovered tight junction claudin-5 and ZO-1 levels.

Detailed procedure: We used intra-peritoneal injection of Streptozotocin (STZ) 65 mg/Kg to 8-week old SD rats to induce diabetics. Three days later, the blood sugar level was over 250 mg/dL, which indicated that diabetics had been successfully induced. Then we intravitreally injected SEMA001 to one eye, and injected placebo (polymet+ negative control microRNA) to the other eye weekly for 4 weeks (FIG. 2). On day 30 Evens blue was intravenously injected to test for extravasation in the eyes. In addition, tight junction and neovascularization markers were also measured. The data are shown in FIGS. 3a-3f.

4. Topical ocular administration; eye drops

Using the same procedure to induce diabetics, we used topically administered eyedrops to treat diabetic retinopathy. On day 3 after injecting STZ, we confirmed the onset of diabetics. On day 4, we used eyedrops twice a day for 30 days. One eye received SEMA001 eyedrop and the other eye received placebo. On the last day of treatment, we intra-venously injected Evens blue to test for extravasation in the eyes. In addition, tight junction and neovascularization markers were also measured. The data are shown in FIG. 5a-5f. We subsequently validated this method of topical ocular delivery of miR-195 using alternative carriers, including alternative polymets, liposome vehicles, jetPEI™ is a linear polyethylenimine.

5. Topical ocular administration; hydrogel lens

Using the same procedure to induce diabetics, this study uses hydrogel lenses to treat diabetic retinopathy. On day 3 after injecting STZ, the onset of diabetics is confirmed, and on day 4, rats are fitted with EW lotrafilcon A (CIBA Vision, Duluth, Ga.) hydrogel lenses (Dk/t 175 barrers/cm); the left eye lens loaded with SEMA001, the right eye serving as a control. Loading protocol: 24 hr RT incubation in 10 uM SEMA001. On the last day of treatment (day 30), we intra-venously inject Evens blue to test for extravasation in the eyes. In addition, tight junction and neovascularization markers are also measured. Results are consistent with topical delivery by eyedrops.

6. Release of miR-195 from contact lenses using an in vitro eye model

We selected four conventional hydrogel (CH) CLs (nelfilcon A [Alcon, Fort Worth, Tx.], omafilcon A [CooperVision, Pleasanton, Calif.], etafilcon A [Johnson & Johnson, New Brunswick, N.J.], and ocufilcon B [CooperVision]) and three silicone hydrogel (SH) lenses (somofilcon A [CooperVision], narafilcon A [Johnson & Johnson], and delefilcon A [Alcon]). All lenses have a dioptric power of −3.00 with a base curve of 8.6 mm Nine lenses of each type are incubated in 10 uM SEMA001 (supra) for 24 hours. The experimental design, eye model, and drug release measurements are consistent with that describe by Phan et al., Transl Vis Sci Technol. 2016 Nov.; 5(6): 3. All nine lenses show good and consistent release kinetics over the 24-hour testing period.

The invention claimed is:

1. A method of treating a diabetic retinopathy or a wet type adult macular degeneration, the method comprising topically delivering to the eye a formulation comprising a micro-RNA 195 and a particle or a vesicle for packaging in or on the micro-RNA 195, wherein the particle or the vesicle is a PEI conjugate that is a conjugation of linear polyethylenimine (PEI) with dicyandiamide to form polymetformin.

2. The method of claim 1, wherein micro-RNA 195 is at a concentration of 0.1-1000 or 1-100 µM.

3. The method of claim 1, wherein the formulation is in the form of an ophthalmic gel, ointment, suspension or solution.

4. The method of claim 1, wherein the formulation is in the form of a polymeric solid or semi-solid formulation selected from a membrane or lens, wafer or microspheres.

5. The method of claim 1, wherein the formulation is in the form of a polymeric solid or semi-solid formulation that is a hydrogel contact lens.

6. The method of claim 1, wherein the formulation is in unit dosage form, and the unit dosage form is a loaded contact lens, eye drop, depot or bollus.

7. The method claim of 1, wherein the formulation is packaged in an eye drop dispenser.

8. The method claim of 1, wherein the formulation further comprises excipients and features suitable for direct, topical delivery to the eye, selected from the group consisting of opthalmically suitable clarity, pH buffer, tonicity, viscosity, stability and sterility.

9. The method claim of 1, wherein the formulation further comprises another, different anti-retinopathy or anti-VEGF drug.

* * * * *